US006596756B1

(12) United States Patent
Goldstein et al.

(10) Patent No.: US 6,596,756 B1
(45) Date of Patent: *Jul. 22, 2003

(54) TREATMENT OF FIBROMYALGIA

(75) Inventors: David Joel Goldstein, Indianapolis, IN (US); Smriti Iyengar, Carmel, IN (US); Rosa Marie Ademe Simmons, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/786,836

(22) PCT Filed: Sep. 10, 1999

(86) PCT No.: PCT/US99/20986

§ 371 (c)(1),
(2), (4) Date: Mar. 9, 2001

(87) PCT Pub. No.: WO00/15223

PCT Pub. Date: Mar. 23, 2000

(30) Foreign Application Priority Data

Sep. 9, 1999 (DE) .......................................... 199 31 989

(51) Int. Cl.[7] ............................................. A61K 31/38
(52) U.S. Cl. ...................................................... 514/438
(58) Field of Search .......................................... 514/438

(56) References Cited

U.S. PATENT DOCUMENTS

| | | | |
|---|---|---|---|
| 5,023,269 A | | 6/1991 | Robertson et al. |
| 5,508,276 A | | 4/1996 | Anderson et al. |
| 5,552,429 A | | 9/1996 | Wong et al. |
| 5,945,416 A | * | 8/1999 | Shannon et al. ............ 514/220 |

FOREIGN PATENT DOCUMENTS

| | | |
|---|---|---|
| WO | WO 96/12485 | 5/1996 |
| WO | WO 97/33880 | 9/1997 |
| ZA | 93/0694 | 7/1993 |

* cited by examiner

Primary Examiner—Rebecca Cook
(74) Attorney, Agent, or Firm—Arvie J. Anderson

(57) ABSTRACT

A method of using N-methyl-3-(1-naphthalenyloxy)-3-(2-thienyl)propanamine to treat persistent pain.

2 Claims, No Drawings

TREATMENT OF FIBROMYALGIA

This is a 371 of PCT/US99 filed Sep. 10, 1999.

The invention relates to a method for using N-methyl-3-(1-naphthalenyloxy)-3-(2-thienyl)propanamine (hereinafter referred to as "duloxetine") for the treatment of persistent pain.

For some years, it has been recognized that the chemistry of serotonin and norepinephrine are extremely important in neurological processes, and pharmacologists and medical researchers have been very actively studying the mechanisms of those neurotransmitters in the brain. Concomitantly, the synthesis and study of pharmaceuticals which affect serotonin and norepinephrine processes in the brain are of great interest and are also being intensively studied, both by pharmaceutical chemists and by medical researchers as well.

Duloxetine inhibits the reuptake of both serotonin and norephinephrine, and is being investigated for use as an antidepressant. 3-aryloxy-3-substituted propanamines, such as duloxetine, have been disclosed in U.S. Pat. No. 5,023,269 as being useful for the treatment of pain. This patent, however, does not specify what forms of pain are treated. PCT/US95/13289 discloses that duloxetine is useful for the treatment and prevention of neuropathic pain and migraine. As stated therein, "Neuropathic pain, as distinct from other varieties of pain, emanates specifically from a neurologic source, as from a nerve which is unnaturally stressed, compressed or otherwise injured, it does not include pain emanating from an injury or inflammation of bone, muscle or other tissue." PCT/US95/13289 defines migraine "as a headache, particularly a very severe headache, which occurs repetitively in patients subject to the condition. It has been treated with partial success with vasoconstrictors but no treatment of migraine in the prior art is reliably successful."

For clinical purposes, pain may be divided into two categories: acute pain and persistent pain. Acute pain is provoked by noxious stimulation produced by injury and/or disease of skin, deep somatic structures or viscera, or abnormal function of muscle or viscera that does not produce actual tissue damage. On the other hand, persistent pain can be defined as pain that persists beyond the usual course of an acute disease or a reasonable time for an injury to heal or that is associated with a chronic pathologic process that causes continuous pain or the pain recurs at intervals for months or years. If pain is still present after a cure should have been achieved, it is considered persistent pain. For the purpose of the present invention, persistent pain can be chronic non-remitting or recurrent. The difference in definition between acute and persistent pain is not merely semantic but has an important clinical relevance. For example, a simple fracture of the wrist usually remains painful for a week to 10 days. If the pain is still present beyond the typical course of treatment, it is likely that the patient is developing reflex sympathetic dystrophy, a persistent pain syndrome that requires immediate effective therapy. Early and effective intervention potentially prevents the undue disability and suffering, and avoids the potential development of a condition that becomes refractory to therapy.

Acute and chronic pain differ in etiology, mechanisms, pathophysiology, symptomatology, diagnosis, therapy, and physiological responses. In contrast to the transitory nature of acute pain, persistent pain is caused by chronic pathologic processes in somatic structures or viscera, by prolonged and sometimes permanent dysfunction of the peripheral or central nervous system, or both. Also, persistent pain can sometimes be attributed to psychologic mechanisms and/or environmental factors.

Persistent pain is a disease state that is one of the most important health problems in industrialized nations throughout the world. Persistent pain and suffering, regardless of cause, has serious physical, behavioral, mental, psychologic, social, and economic effects on both the patient and the family, and is very costly to society.

The mental effects of prolonged or persistent pain are greatly influenced by the duration, intensity, and periodicity of the persistent pain, by the personality and psychologic makeup of the individual, and by various socioloaic and economic factors. The duration of the persistent pain is an important factor in determining the mental effects; for while the average individual can briefly bear, both psychologically and physiologically, even the most severe pain, if such pain is prolonged it exerts effects which cause mental and physical deterioration. Prolonged, persistent, and intense pain interferes with thought processes and dominates the entire organism.

The impact of persistent pain on society is equally devastating as its effects on the sufferer. Patients develop problems with their families and friends, and, as previously mentioned, decrease their social interactions. Household chores (cooking, caring for a sick child, etc.), social and familial obligations are frequently cancelled. Some patients are unable to work, some are ineffective at work, others are encouraged not to work, and still others lose their jobs because of frequent absences. In fact, the unemployment rate of some chronic pain conditions can be 4–5 times higher than the average unemployment rate in the United States. These profound societal effects may render the patient an economic liability rather than an asset.

Current therapies for persistent pain include opiates, barbiturate-like drugs such as thiopental sodium and surgical procedures such as neurectomy, rhizotomy, cordotomy, and cordectomy. These therapies have significant drawbacks. Opiates and barbiturate-like drugs have limiting side effects and are addictive. Tricyclic antidepressants and anticonvulsants are marginally effective, and also are associated with some limiting side effects. Electrical stimulation, e.g., TENS has limited success in chronic pain. Surgical procedures are expensive, irreversible and often fail to provide long-term relief from persistent pain. Faced with suboptimal therapy for persistent pain, the patient suffers more, complains more, and becomes more desperate and dissatisfied with their healthcare. As a consequence, the patient seeks and consumes more direct and indirect healthcare resources.

In light of these realities, there is a demand for more effective analgesic agents, targeted specifically for persistent pain, which have a superior safety and tolerability profile and are non-addictive. The ideal analgesic would reduce the awareness of pain, produce analgesia over a wide range of pain types, act satisfactorily whether given orally or parenterally, produce minimal or no side effects, and be free from a tendency to produce tolerance and drug dependence.

The present invention addresses the need for a safe and effective treatment of persistent pain by providing a method of treating persistent pain.

In accordance with the present invention, there is provided a method of treating persistent pain comprising the administration to a patient in need of such treatment of an effective amount of duloxetine.

The present invention also provides the use of duloxetine for the manufacture of a medicament for treating persistent pain.

Furthermore, the present invention provides the use of duloxetine for treating persistent pain.

The term "treating" for purposes of the present invention, includes prophylaxis or prevention, amelioration or elimination of a named condition once the condition has been established.

The term "patient" for purposes of the present invention is defined as any warm blooded animal such as, but not limited to, a mouse, guinea pig, dog, horse, or human. Preferably, the patient is human.

For purposes of the present invention, the term "acute pain" is defined as pain which is provoked by noxious stimulation produced by injury and/or disease of skin, deep somatic structures or viscera, or abnormal function of muscle or viscera that does not produce actual tissue damage.

The term "persistent pain" as used herein, is defined as pain that persists beyond the usual course of an acute disease or a reasonable time for an injury to heal or that is associated with a chronic pathologic process that causes continuous pain or the pain recurs at intervals for months or years. If pain is still present after a cure should have been achieved or beyond a typical course of treatment, it is considered persistent pain. The length of time that must pass before pain is persistent depends upon the nature of the pain and the typical course of treatment associated with the pain. Pain is persistent if it lasts beyond a typical course of treatment.

Persistent pain includes, but is not limited to, tension-type headache, musculoskeletal pain, pain associated with somatoform disorders, visceral pain, painful diabetic neuropathy, vascular pain, arthritic pain, back pain, neck pain, shoulder pain, cancer pain, pain associated with AIDS, postoperative pain, and post-burn pain.

Duloxetine is effective in treating persistent pain as defined above. Also, duloxetine is useful in treating other conditions where there is hyper-sensitization to painful signals, hyperalgesia, allodynia, enhanced pain perception, and enhanced memory of pain. Duloxetine will improve coping with pain.

Tension-type headache is the most common form of primary or idiopathic headaches, i.e. those that are not related to an identifiable cause. Two types of tension-type headaches are recognized; episodic tension-type and chronic tension-type. "Chronic tension-type headache" as used herein, is defined by International Headache Society criteria (Cephalalgia 1988;8 (Suppl 7): 1–96) as recurrent headaches that are "present for at least 15 days a month during at least 6 months. The headache is usually pressing/tightening in quality, mild or moderate in severity, bilateral and does not worsen with physical activity. Nausea, photophobia or phonophobia may occur."

Chronic tension-type headache (TTH) occurs in 2–3% of the population. The severity of the pain of TTH, unlike that of episodic TTH, is usually moderate to severe. Chronic TTH is differentiated from migraine clinically based on the following features: bilaterality of pain; non-pulsating quality; often varying locations of pain; seldom association with both light (photophobia) and noise (phonophobia) sensitivity. In addition, smell sensitivity (osmophobia) is not a symptom of TTH; absence of neurological accompaniments such as visual or sensory auras.

"Somatoform disorders," as used in the present invention, are defined as having, as a common feature, the presence of physical symptoms that suggest a general medical condition which are not fully explained by a general medical condition, by the direct effects of a substance, or by another mental disorder. (*Diagnostic and Statistical Manual of Mental Disorders*, 4$^{th}$ edition, p. 445). Somatoform disorders include functional somatic syndromes, including those referenced in Barsky A J, Borusn J F. *Functional Somatic Syndromes*. Ann Intern Med 1999;130:910–921, such as, but not limited to, multiple chemical sensitivity, sick building syndrome, repetition stress injury, chronic whiplash, chronic lime disease, side effects of silicon breast implants, candidiasis hypersensitivity, the Gulf War Syndrome, food allergies, mitral valve prolapse, and hypoglycemia.

The term "musculoskeletal pain" as used herein, includes, but is not limited to, myofascial pain, trauma-induced pain, and chronic regional pain syndrome.

The term "myofascial pain" as used herein, includes, but is not limited to, temporo-mandibular joint disease (TMJ) and fibromyalgia with or without chronic fatigue syndrome. The term "fibromyalgia", for purposes of the present invention, includes, but is not limited to, that pain which is defined by the American College of Rheumatology (ACR) classification (Wolf F, et al., The American College of Rheumatology 1990 criteria for the classification of fibromyalgia: Report of the Multicenter Criteria Committee. Arthritis Rheum 33:160–172;1990.) Fibromyalgia is a clinical syndrome characterized by chronic muscle aches, stiffness, fatigue, non-restorative sleep, and localized tender points. The ACR criteria for fibromyalgia are: 1) widespead aching in all four quadrants and in the axial skeleton for more than least 3 months in duration; and 2) pain in 11 or more of 18 tender points under digital pressure examination.

For the purposes of the present invention, "painful diabetic neuropathy" is pain which is secondary to injury to nerves as a complication of diabetes mellitus. Injury to nerves in diabetes mellitus is caused, at least in part, by decreased blood flow and high blood-sugar levels. Some diabetics will not develop neuropathy, while others may develop this condition relatively early. Diabetic neuropathies may be classified into mononeuropathies involving one or more focal sites and generalized polyneuropathies which may be diffuse, symmetric and often predominantly involving sensory modalities [Merrit's Textbook of Neurology, 9th ed., ed by L. P. Rowland, Williams and Wilkins, 1995, p. 669]. Manifestations of diabetic neuropathy can include dysfunction of autonomic nerves resulting in dysregulation of vital functions including the heart, smooth muscles, and glands. Low blood pressure, diarrhea, constipation, and sexual impotence also result from autonomic neuropathies. Cranial neuropathies may affect vision. Sensory neuropathies affect the nerves that carry sensory information from the skin and other sense organs to the brain. Loss of sensation of touch, pressure, vibration and temperature to a body part or area may result from sensory neuropathies. Diabetic neuropathies are sometimes, but not always, accompanied by pain. Painful diabetic neuropathy tends to develop in stages. Early on, intermittent pain and tingling may be noted in the extremities of nerve terminal fields, particularly the feet in the case of autonomic or sensory neuropathy, or in the face and around the eye in the case of cranial neuropathy. In later stages, the pain is more intense and constant. Finally, a painless neuropathy develops when pain sensation is lost to an area, which greatly increases the risk of severe tissue injury without pain as an indicator of injury."

The term "visceral pain" includes, but is not limited to that pain associated with irritable bowel syndrome (IBS) with or without chronic fatigue syndrome (CFS), inflammatory bowel disease (IBD), and interstitial cystitis.

The term "vascular pain", for purposes of the present invention, is that pain "produced by one or more of the following pathophysiologic factors: (a) inadequate perfusion of tissues with consequent transient or continuous ischemia such as occurs in the muscles of the limb during exercise, ischemia of the skin that produces rest pain, and ischemia of a viscus such as the heart or gastrointestinal tract; (b) secondary changes such as ulcerations or gangrene in the skin or abdominal viscera; (c) sudden or accelerated changes in the vascular dimension of large vessels such as occurs with aneurysm; (d) rupture of the aorta with consequent spillage of blood that stimulates nociceptive fibers in the parietal peritoneum or parietal pleura; (e) intense spasm consequent to the intra-arterial injection of severe irritant on the endothelium of the artery; and (f) impairment of venous return with consequent massive edema that rapidly stretches fascial compartments". (J. J. Bonica et al., The Management of Pain Vol. 1 (2nd ed., Philadelphia: Lea & Febiger, 1990.) Examples include, but are not limited to, arteriosclerosis obliterans, thromboangitis obliterans, acute arterial occlusion, embolism, congenital arteriovenous aneurysm, vasospastic disease, Raynaud's disease, acrocyanosis, acute venous occlusion, thrombophlebitis, varicose veins, and lymphedema.

The term "arthritic pain" includes, but is not limited to, osteoarthritis, rheumatoid arthritis, ankylosing spondylitis, Reiter's syndrome, psoriatic arthritis, gout, pseudogout, infectious arthritis, tendonitis, bursitis, bone lesions and joint soft tissue inflammation.

For purposes of the present invention, "nociceptive pain" is pain caused by a tissue-damaging process that excites nociceptive afferents or pain which is provoked by prolonged excitation of nociceptors. Persistent pain which arises from nociceptive pain may be due to persistent noxious stimulation of nociceptors or their sensitizations or both, or they may be initiated by these factors and prolonged by their persistence, by various reflex mechanisms and by other factors.

The term "nociception" as used herein refers to the neural mechanisms by which noxious stimuli are detected. Nociception involves two steps: transductions of noxious stimuli by peripheral nerve endings and transmission of these signals to the central nervous system.

The present invention is useful for the treatment of nociceptive pain or pain that arises from a combination of nociceptive and neuropathic etiologies. It is preferred that the pain to be treated is nociceptive pain.

It is also believed by those of ordinary skill in the art that central sensitization contributes to the expression of persistent pain. The term "central sensitization" as used herein is defined as hyperexcitability of spinal neurons.

Duloxetine, N-methyl-3-(1-naphthalenyloxy)-3-(2-thienyl)propanamine, is usually administered as the hydrochloride salt and as the (+) enantiomer. It was first taught by U.S. Pat. No. 4,956,388, which shows its high potency in the inhibition of serotonin and norepinephrine uptake. The term "duloxetine" as used herein, refers to any acid addition salt or the free base of the molecule.

Duloxetine is a safe drug, and its use in the treatment of persistent pain is a superior treatment because of its improved safety. The compound is particularly selective, having few if any physiological effects besides those on norepinephrine and serotonin processing, and therefore is free of side effects and unwanted activities, unlike the limiting side effects of other similar drugs used for the treatment of persistent pain. Further, it is effective at relatively low doses, as discussed below, and may safely and effectively be administered once per day. Thus, difficulties created by the multiple dosing of patients are completely avoided.

The effective amount or dose of duloxetine for treating persistent pain is in the range from about 1 mg/day to about 200 mg/day. The preferred adult dose is in the range from about 40 to about 150 mg/day, and a more highly preferred adult dose is from about 60 to about 120 mg/day. The optimum dose for each patient, as always, must be set by the physician in charge of the case, taking into account the patient's size, other medications which the patient requires, severity of the persistent pain and all of the other circumstances of the patient.

Since duloxetine is readily orally absorbed and requires only once/day administration, there is little or no reason to administer it in any other way than orally. It is produced in the form of a clean, stable crystal, and thus is easily formulated in the usual oral pharmaceutical forms, such as tablets, capsules, suspensions, and the like. The usual methods of pharmaceutical scientists are applicable. It may usefully be administered, if there is any reason to do so in a particular circumstance, in other pharmaceutical forms, such as, but not limited to, injectable solutions, depot injections, suppositories and the like, which are well known to and understood by pharmaceutical scientists. It will substantially always be preferred, however, to administer duloxetine as a tablet or capsule and such pharmaceutical forms are recommended.

A preferred duloxetine enteric formulation as disclosed in U.S. Pat. No. 5,508,074, which is hereby incorporated by reference, is a pellet formulation comprising a) a core consisting of duloxetine and a pharmaceutically acceptable excipient; b) an optional separating layer; c) an enteric layer comprising hydroxypropylmethylcellulose acetate succinate (HPMCAS) and a pharmaceutically acceptable excipient; d) an optional finishing layer. The following example demonstrates the preparation of a preferred such formulation.

EXAMPLE

| 10 mg Duloxetine base/capsule Bill of Materials | |
| --- | --- |
| Beads | |
| Sucrose-starch nonpareils, 20–25 mesh | 60.28 mg |
| Duloxetine layer | |
| Duloxetine | 11.21 mg |
| Hydroxypropylmethylcellulose | 3.74 mg |
| Separating layer | |
| Hydroxypropylmethylcellulose | 2.51 mg |
| Sucrose | 5.00 mg |
| Talc, 500 mesh | 10.03 mg |
| Enteric layer | |
| HPMCAS, LF grade, Shin-Etsu Chemical Co., Tokyo, Japan | 25.05 mg |
| Triethyl citrate | 5.00 mg |
| Talc, 500 mesh | 7.52 mg |
| Finishing layer | |
| Hydroxypropylmethylcellulose | 8.44 mg |
| Titanium dioxide | 2.81 mg |
| Talc | Trace |
| | 141.60 mg |

The duloxetine layer was built up by suspending duloxetine in a 4% w/w solution of the hydroxypropylmethylcellulose in water, and milling the suspension with a CoBall Mill (Fryma Mashinen AG, Rheinfelden, Switzerland)

model MS-12. A fluid bed dryer with a Wurster column was used to make this product, at a batch size of 1.0 kg. The separating layer was added from a 4% w/w solution of the hydroxypropyl-methylcellulose in water, in which the sucrose was also dissolved.

In order to prepare the enteric coating suspension, purified water was cooled to 10° C. and the polysorbate, triethyl citrate and silicone emulsion were added and dispersed or dissolved. Then the HPMCAS and talc were added and agitated until homogeneity was obtained, and the HPMCAS was fully neutralized by addition of ammonium hydroxide until solution of the polymer was complete. To this suspension, a carboxymethylcellulose aqueous solution, 0.5% w/w, was added and blended thoroughly. The enteric suspension was maintained at 20° C. during the coating process. The enteric suspension was then added to the partially completed pellets in the Wurster column at a spray rate of about 15 ml/min, holding the temperature of the inlet air at about 50° C. The product was dried in the Wurster at 50° C. when the enteric suspension had been fully added, and then dried on trays for 3 hours in a dry house at 60° C. A finishing layer was then applied which consisted of a 4.5% w/w/hydroxypropylmethyl-cellulose solution containing titanium dioxide and propylene glycol as plasticizer. The pellets were completely dried in the fluid bed dryer and then were then filled in size 3 gelatin capsules.

Example I

The analgesic effect of duloxetine for the treatment of persistent nociceptive pain was demonstrated using the well-known "formalin test." The formalin test is a model of persistent nociceptive activation induced by tissue injury which can lead to central sensitization. (Shibata, M., Ohkubo, T., Takahashi, H., and Inoki, R., "Modified formalin test: Characteristic biphasic pain response," Pain (1989) 38: 347–352; and Tjolsen, A., Berge, O. G., Hunskaar, S., Rosland, J. H., and Hole, K., "The formalin test: an evaluation of the method," Pain (1992) 51:5–17.) The effect of duloxetine on formalin-induced paw-licking behavior in the rat was investigated as an index of persistent nociceptive activation. In this test, the injection of formalin under the skin on the dorsal lateral surface of the hind paw of rats causes an immediate and intense increase in the spontaneous activity of C fiber afferents. This activation evokes a distinctly quantifiable behavior indicative of pain, such as licking, flinching, shaking or biting of the injected paw. The behavioral response to formalin is biphasic, with an early phase that is short lived, followed by an extended tonic response or late phase of persistent nociceptive activation. Mechanisms causing the late phase response, such as central sensitization of pain transmitting neurons, are currently believed to contribute to various types of persistent pains.

Male Sprague-Dawley rats (200–250 g; Charles River, Portage, Mich.) were maintained at constant temperature and light (12 h light/12 h dark) for 4–7 days prior to the studies. Animals had free access to food and water at all times prior to the day of the experiment.

The formalin test was performed in custom made Plexiglas® boxes 25×25×20 cm (length×width×height) in size. A mirror placed at the back of the box allowed the unhindered observation of the formalin injected paw. Rats were acclimatized individually in the cubicles at least 1 hour prior to the experiment. All testing was conducted between 08:00 and 14:00 hr and the testing room temperature was maintained at 21–23° C. Test compound was administered 30 or 60 minutes prior to the formalin injection. Formalin (50 μl of a 5% solution in saline) was injected subcutaneously into the dorsal lateral surface of the right hind paw with a 27 gauge needle. Observation started immediately after the formalin injection. Formalin-induced pain was quantified by recording in 5 minute intervals the number of formalin injected paw licking events and the number of seconds each licking event lasted. These recordings were made for 50 minutes after the formalin injection. After the experiment, animals were killed with an overdose of CO2. (Euthanasia protocol, Eli Lilly Animal Use and Care Committee.)

Scoring in the formalin test was performed according to Coderre et al., 1993b and Abbott et al., 1995. (Coderre T. J., Fundytus M. E., McKenna J. E., Dalal S. and Melzack R. "The formalin test: a validation of the weighted-scores method of the behavioral pain rating," Pain(1993b) 54: 43–50; and Abbott F. V., Franklin K. B. J. and Westbrook R. F. "The formalin test: scoring properties of the first and second phases of the pain response in rats," Pain (1995) 60: 91–102.) The sum of time spent licking in seconds from time 0 to 5 minutes was considered the early phase while the late phase was taken as the sum of seconds spent licking from 15 to 40 minutes.

Data are presented as means with standard errors of means (±SEM). Data were evaluated by one-way analysis of variance (ANOVA) and the appropriate contrasts analyzed by Tukey's test and Dunnett "t" test for two-sided comparisons.

| Treatment | Early Phase | Late Phase |
|---|---|---|
| vehicle (i.p.)* duloxetine(i.p.)* (−30 min) | 31.33 ± 8.04 | 386.22 ± 40.13 |
| 3 mg/kg | 32.78 ± 15.97 | 254.00 ± 45.87 |
| 10 mg/kg | 17.00 ± 5.83 | 163.89 ± 54.14*** |
| 15 mg/kg | 29.56 ± 16.30 | 80.44 ± 36.22*** |
| vehicle (p.o.)** duloxetine(p.o.)** (−60 min) | 10.71 ± 3.17 | 376.71 ± 36.93 |
| 3 mg/kg | 21.78 ± 5.14 | 393.56 ± 26.74 |
| 10 mg/kg | 20.22 ± 5.29 | 255.78 ± 38.22*** |
| 20 mg/kg | 12.67 ± 3.61 | 161.11 ± 31.77*** |

*(i.p.): intraperitoneal
**(p.o.): oral
***$p < 0.05$ significantly different compared to vehicle control of group.

As illustrated above, duloxetine blocks the late phase response to formalin in a dose-dependent manner. These results demonstrate that duloxetine is effective in treating nociceptive pain which is persistent.

Example II

The tendency of duloxetine to induce ataxia or neuromuscular effects at analgesic doses was investigated using the well-known rotorod test.

Male Sprague-Dawley rats (200–250 g; Charles River, Portage, Mich.) were maintained at constant temperature and light (12 h light/12 h dark) for 4–7 days prior to the studies. Animals had free access to food and water at all times prior to the day of the experiment.

An automated accelerating rotorod (Omnitech Electronics Inc., Columbus, Ohio) connected to an IBM PC computer was utilized. For training and testing purposes, the rotorod was set up to accelerate to 17 r.p.m. in 5 seconds and maintaining that speed for 40 seconds. Rats were given 3 training trials to learn to maintain posture on the rotorod prior to the actual day of drug testing. The following day, rotorod testing was conducted both at 30 and 80 minutes for i.p. and at 60 and 110 minutes for p.o. following administration of drug or compound. Animals that maintained posture and did not fall off the rotorod were given a maximum score of 40 seconds.

All data were analyzed using the JMP statistical program. Data are presented as means with standard errors of means (±SEM). Data were evaluated by one-way analysis of variance (ANOVA) and the appropriate contrasts analyzed by Tukey's test and Dunnett "t" test for two-sided comparisons.

| Treatment | Ataxia score, 30 mins after drug, i.p.* | Ataxia score 80 mins after drug, i.p.* |
|---|---|---|
| vehicle (i.p.)* | 30.99 ± 4.11 | 30.99 ± 4.11 |
| duloxetine(i.p.)* (−30 min) | | |
| 3 mg/kg | 34.27 ± 4.02 | 33.35 ± 3.23 |
| 10 mg/kg | 29.42 ± 6.71 | 26.07 ± 6.24 |
| 30 mg/kg | 24.75 ± 6.88 | 25.52 ± 5.89 |

| Treatment | Ataxia Score, 60 mins after drug, p.o.** | Ataxia score 110 mins after drug, p.o.** |
|---|---|---|
| vehicle (p.o.)** | 38.68 ± 1.97 | 38.68 ± 1.97 |
| duloxetine(p.o.)** (−60 min) | | |
| 3 mg/kg | 40.00 ± 0.00 | 40.00 ± 0.00 |
| 10 mg/kg | 39.11 ± 0.89 | 39.56 ± 0.44 |
| 20 mg/kg | 40.00 ± 0.00 | 40.00 ± 0.00 |

*(i.p.): Intraperitoneal
**(p.o.): oral

As demonstrated above, duloxetine did not show ataxia or neuromuscular effects in the rotorod test at doses that caused analgesia.

Example III

The analgesic effect of duloxetine for the treatment of neuropathic pain is demonstrated using the well-known "Seltzer Model" which involves partial ligation of the sciatic nerve. (Seltzer, Z., Dubner, R. and Shir, Y., "A novel behavioral model of neuropathic pain disorders produced in rats by partial sciatic nerve injury," Pain, 43 (1990) 205–218.) This model mimics the major clinical symptoms of causalgia, which are rapid onset of hyperalgesia and allodynia.

Young adult male Sprague Dawley rats from Harlan (Indianapolis, Ind.) weighing 135–155 g were housed in groups of 3–4 in plastic cages with soft bedding under a 12/12 h day/night cycle. Rats were placed in a prone position under gaseous isofluorane anesthesia. Surgery was performed on the left upper thigh as described by Seltzer et al., 1990. The sciatic nerve was carefully exposed by separating the muscles above it with a small retractor. The dorsal third to half of the nerve was tightly ligated with a 4.0 silk suture at a sight distal to the point at which the posterior biceps-semitendinosus nerve branches off. The wound site was sutured back according to animal protocol procedures. Animals were then allowed to recover and placed back into their cages. The rats recovered sufficiently from the surgical procedures to resume normal activity within 30 min after termination of the gaseous anesthesia.

Beginning at 24 hours following recovery from surgery, the pain sensitivity of the hind paw was analyzed using von Frey filaments applied to both the surgical and contralateral paw surfaces. In this method, a brisk foot withdrawal in response to normally innocuous mechanical stimuli was measured. (Kim, S. H. and Chung, J. M., "An experimental model for peripheral neuropathy produced by segmental spinal nerve ligation in the rat," Pain, 50 (1992) 355–363.) Innocous mechanical stimuli were applied with von Frey filaments of different bending forces (corresponding to grams of force ranging from 1–15 g). The rat was placed in a plexiglass box with a metal mesh floor and the von Frey filaments were applied to the plantar surface of the foot. A von Frey filament was applied perpendicular to the plantar surface with sufficient force to cause slight bucking against the paw, and held for 2–3 seconds to each hind paw. A positive response is noted if the paw is sharply withdrawn. The threshold (gram force) to cause foot withdrawals in response to the filament was expressed as Response (g) and calculations to arrive at this were based on the method of Dixon, W. J., Efficient analysis of experimental observations, Ann. Rev. Pharmacol. Toxicol. 20:441–462, 1980. Stimulation of normal human skin with the weak (4.3 nM) and strong (5.18 nM) von Frey filaments elicits respectively, a weak sense of touch and a sense of pressure. Therefore, a significant change in the sensory threshold causing brisk foot withdrawals in response to these innocuous mechanical stimuli is due to development of mechanical allodynia due to the nerve ligation. The response (g) (mechanical stimuli) was plotted against test doses of drug or vehicle. While the paw on the surgical side develops mechanical allodynia, the paw on the contralateral non-surgical side remains normal and serves as a control.

All data were analyzed using the JMP statistical program. Data were presented as means with standard errors of means (±SEM). Data were evaluated by one-way analysis of variance (ANOVA) and the appropriate contrasts analyzed by Tukey's test and Dunnett "t" test for two-sided comparisons.

| Treatment | Allodynia Response (g) |
|---|---|
| No nerve ligation | |
| vehicle (i.p.*, p.o.**) | 15 ± 0.0 (no allodynia) |
| Nerve ligation | |
| vehicle (i.p.*) | 2.18 ± 0.31 |
| duloxetine (15 mg/kg, i.p.*, 1 hour pretreatment) | 8.57 ± 1.72*** |
| vehicle (p.o.**) | 3.45 ± 0.56 |
| duloxetine (20 mg/kg, p.o., 1 hour pretreatment) | 8.53 ± 1.66* |
| duloxetine (20 mg/kg × 4 day, p.o., sub-chronic pretreatment) | 9.18 ± 2.95* | intraperitoneal(i.p.)* or oral (p.o.)** and after sub-chronic oral dosing of duloxetine once a day for four consecutive days;
***p < 0.05 significantly different compared to vehicle control of group.

As illustrated above, duloxetine attenuates the allodynia developed following partial ligation of the sciatic nerve after acute or sub-schronic systemic administration. These results demostrate that duloxetine is effective in the treatment of neuropathic pain.

We claim:
1. A method of treating fibromyalgia comprising administering to a patient in need of treatment an effective amount of duloxetine.
2. The method of cliam 1 wherein duloxetine is (+)-N-methyl-3-(1-naphthalenyloxy)-3-(2-thienyl)propanamine hydrochloride.

* * * * *